United States Patent [19]

Melde

[11] Patent Number: 4,512,635
[45] Date of Patent: Apr. 23, 1985

[54] DENTAL MIRROR APPARATUS

[76] Inventor: Chris R. Melde, 7007 Third Ave., Scottsdale, Ariz. 85251

[21] Appl. No.: 337,085

[22] Filed: Jan. 4, 1982

Related U.S. Application Data

[63] Continuation-in-part of Ser. No. 259,659, May 1, 1981, abandoned, which is a continuation-in-part of Ser. No. 93,621, Nov. 13, 1979, abandoned.

[51] Int. Cl.³ .......................... G02B 7/18; A61B 1/24
[52] U.S. Cl. ...................................... 350/640; 433/30
[58] Field of Search ............... 350/307, 308, 300, 582, 350/584, 309; 433/30

[56] References Cited

U.S. PATENT DOCUMENTS

| | | | |
|---|---|---|---|
| 2,336,392 | 12/1943 | Borlo | 350/308 |
| 2,534,706 | 12/1950 | Gittelson | 350/309 |
| 2,582,121 | 1/1952 | Harvey | 350/309 |
| 2,686,456 | 8/1954 | Szuba et al. | 350/308 |
| 3,014,279 | 12/1961 | Fosdal | 350/308 |
| 3,031,930 | 5/1962 | Kafig et al. | 350/308 |
| 3,613,246 | 10/1971 | Zdarsky | 350/308 |
| 3,829,199 | 8/1974 | Brown | 350/308 |
| 3,969,824 | 7/1976 | Widen et al. | 350/584 |

Primary Examiner—Jon W. Henry
Attorney, Agent, or Firm—H. Gordon Shields

[57] ABSTRACT

Dental mirror apparatus includes two reflective surfaces, at least one of which is a front surface mirror and the reflective surfaces are changeable from one surface to the other, and an endodontic tool is built onto the handle of the mirror. The mirror element includes a plurality of attachment elements for securing the mirror element to the handle, and means for draining moisture from the dental mirror surface.

13 Claims, 28 Drawing Figures

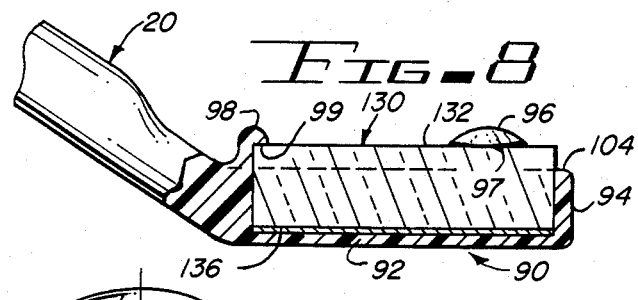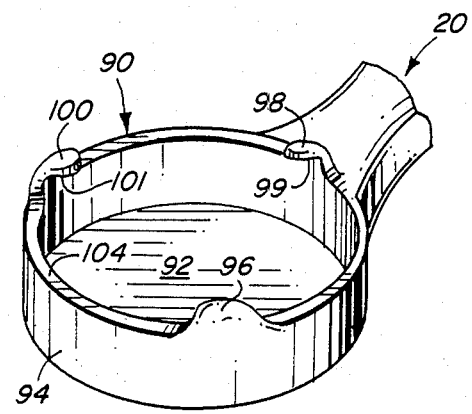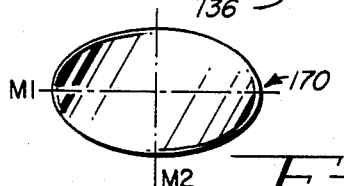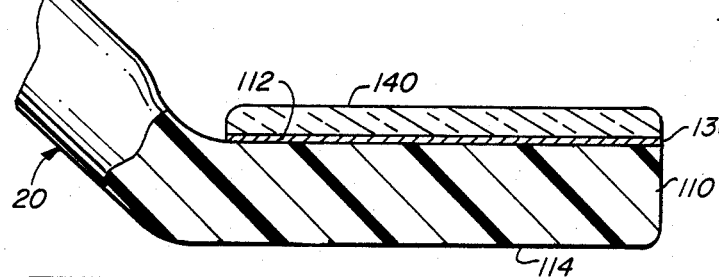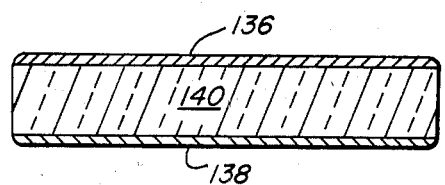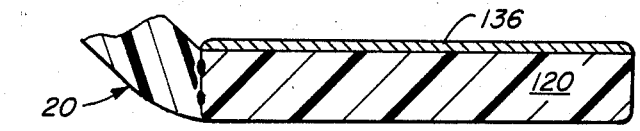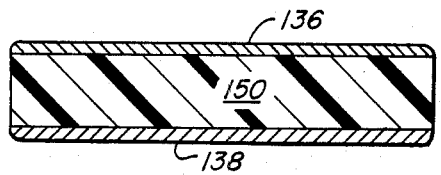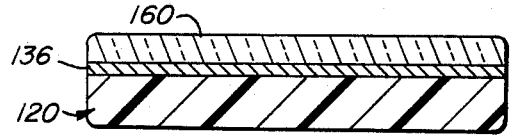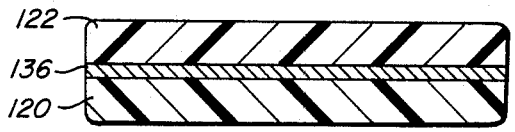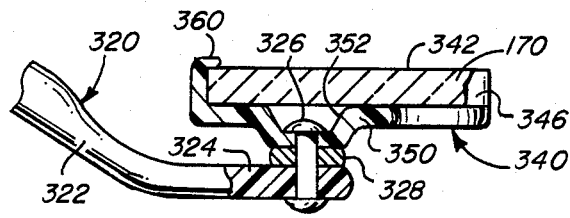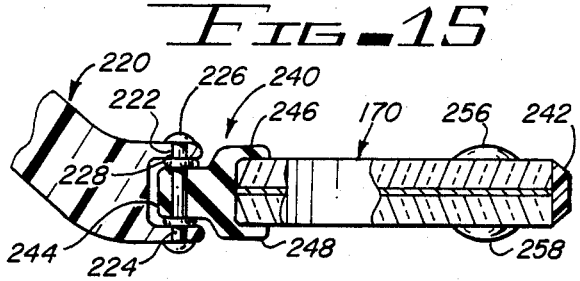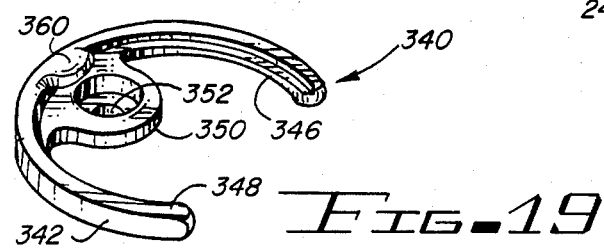

DENTAL MIRROR APPARATUS

REFERENCE TO RELATED APPLICATIONS

This application is a continuation-in-part application of Ser. No. 259,659, filed May 1, 1981, now abandoned; which is a continuation-in-part of Ser. No. 93,621, filed Nov. 13, 1979, also now abandoned.

BACKGROUND OF THE INVENTION

1. Field of the Invention

This invention relates to dental mirrors and, more particularly, to dental mirrors comprising a reversible mirror having two reflective surfaces.

2. Description of the Prior Art

Dental mirrors of the prior art comprise a relatively thin circular glass element having a smooth, planar surface on the top of the glass element, and a reflective coating on the bottom of the glass element. The outer edge of the element is ground. The glass element is typically inserted into a metal or a plastic socket. The socket includes an edge which is crimped around the outer periphery of the mirror at the ground area to hold or retain the glass mirror element in the socket. The ground area is an area which slopes away from the mirror surface to allow the crimped portion of the socket to firmly grasp the mirror element.

The ground area of the glass, where the glass is held into a socket, is not smooth, does not comprise a smooth, planar surface, and accordingly is pitted. The pitted sloping side accordingly collects dirt, debris, and blood, which are very difficult to remove by ordinary cleaning processes. Germs from a patient's mouth which get onto the ground area of the mirror may become deeply imbedded into the pitted area and accordingly may survive autoclave sterilization.

When the top or upper surface of the glass is scratched, the entire mirror apparatus is unusable and is accordingly thrown away. This represents an economic loss, since the mirror cannot be reversed so as to use the other side.

With the reflective or mirror coating on the bottom surface of the glass, the mirror is referred to as a plane surface mirror. The reflection in the mirror is through the glass, which represents a substantial distance, typically at least sixty thousandths of an inch, that the dentist is viewing from, or through, as he uses the mirror. That is, the closest that the dentist can get with a mirror to a tooth is at least the thickness of the glass mirror element.

Furthermore, there are occasions when it is desirable for a dentist to view in opposite directions substantially simultaneously. For doing so, a double surface mirror would be advantageous. With the mirror apparatus of the prior art, the glass element alone comprises the mirror, and accordingly the apparatus must be reversed and repositioned in order to allow viewing in opposite directions. A more desirable situation is a front surface mirror, with the reflective surface no more than ten or fifteen thousandths of an inch from the surface of the element.

There are two types of handles used with prior art dental mirrors, one of which is metal and one of which is plastic. The plastic handled apparatus is preferred for cost purposes since the cost of such plastic handles is less than the cost of metal handles. However, the metal mirror handles are preferred for endodontic testing purposes. That is, with the heavier, more dense metal handles, a dentist may reverse the mirror and use the handle of the mirror as an endodontic tool. The lighter, less dense plastic handle cannot be used in such a manner.

The above paragraphs generally discuss a typical dental mirror of the prior art and some of its shortcomings. In addition to the general description given above, the prior art also includes several patents. One such patent is U.S. Pat. No. 3,300,859, which discloses a pair of glass mirror elements to produce a double mirror. However, both mirrors comprise plane surface mirrors and the reflection in each mirror is viewed through the thickness of its glass element. A frame, having arcuate indentations, is fixed to the mirror elements, and the mirror elements cannot be reversed when one becomes scratched.

U.S. Pat. No. 3,539,247 discloses a dental mirror including a housing having a reflective element which includes a belt or film which may be changed or cleaned by rolling an adjacent portion of the belt or film to take the place of the original portion. A reflective surface is disposed beneath the belt or film. A wetting agent is disposed within the housing, and sealing members are used to prevent the wetting agent from leaking out of the housing and to act as a squeegee as the film or belt is rolled.

U.S. Pat. No. 3,638,013 discloses a combination light and mirror apparatus in which fiber optics are used to transmit light to a dental mirror. For the mirror, a glass element is used, in one embodiment, and plastic, such as lucite, is used in another embodiment. However, all of the mirror elements include reflective surfaces remote from the planar mirror surfaces, typical of the prior art.

U.S. Pat. No. 3,829,199 discloses disposable dental mirror apparatus, which includes a removable mirror element secured to a handle. The mirror element includes only a single reflective coating disposed on the bottom of a plastic disc, and the disc is secured within a base. The disc and base comprise the disposable portion of the dental mirror apparatus.

U.S. Pat. No. 3,468,030 discloses a triangular shaped flexible mouth prop which fits into the mouth between the cheek and the teeth to block the parotid gland. The apparatus includes absorbent material on one side and a foil strip on the other side for reflecting light.

SUMMARY OF THE INVENTION

The dental mirror apparatus described and claimed herein comprises a pair of reversible mirror elements, at least one mirror element of which comprises a front surface mirror, and which is reversible to allow using the second mirror element if or when the surface of the first mirror element becomes scratched, and the socket holding the double mirror element is made of plastic with a metal tip or end usable as an endodontic tool.

Among the objects of the present invention are the following:

To provide new and useful dental mirror apparatus;

To provide new and useful dental mirror apparatus including a pair of reversible mirror elements;

To provide new and useful dental mirror apparatus including a front surface mirror;

To provide new and useful dental mirror apparatus which includes an endodontic tool on the mirror handle;

To provide new and useful inexpensive and lightweight dental mirror apparatus; and To provide new and useful dental mirror apparatus having a replaceable mirror element.

BRIEF DESCRIPTION OF THE DRAWING

FIG. 8 is a side view in partial section of an alternate embodiment of the mirror apparatus of the present invention.

FIG. 9 is a perspective view of the holder and handle element of the embodiment of FIG. 8.

FIG. 10 is a view in partial section of another alternate embodiment of the mirror apparatus of the present invention.

FIG. 11 is a view in partial section illustrating another alternate embodiment of the apparatus of the present invention.

FIGS. 12, 13, 14, and 15 comprise views in partial section of alternate embodiments of mirror elements of the present invention, illustrating various types of material usable to provide reversible dental mirror elements.

FIG. 16 is a perspective view of an elongated or elliptical mirror element which may be used with the apparatus of the present invention.

FIG. 17 is a view in partial section of the apparatus of the present invention utilizing a swivel connection between the handle and the mirror element and its holder or socket.

FIG. 18 is a view in partial section of an alternate embodiment of the swivel apparatus of FIG. 17.

FIG. 19 is a top view of a portion of the apparatus of FIG. 18.

DESCRIPTION OF THE PREFERRED EMBODIMENT

Figure 1:
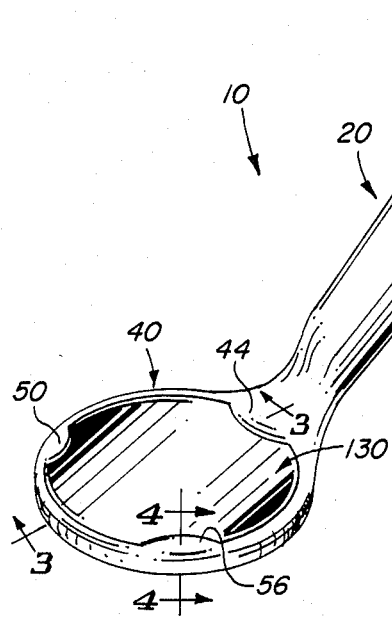
FIG. 1 is a perspective view of dental mirror apparatus embodying the present invention.
Figure 2:
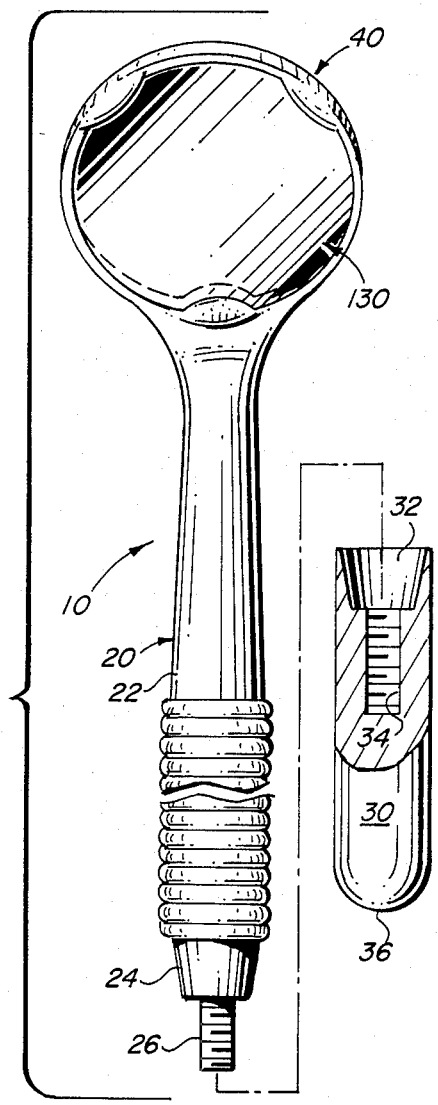
FIG. 2 is a top view of apparatus of the present invention.
Figure 3:
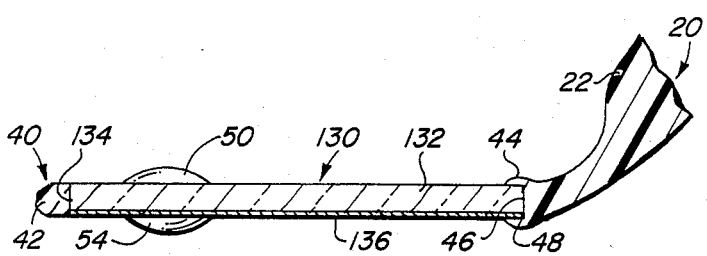
FIG. 3 is a view in partial section of the dental mirror apparatus of FIG. 1, taken generally along line 3—3 of FIG. 1.
Figure 4:
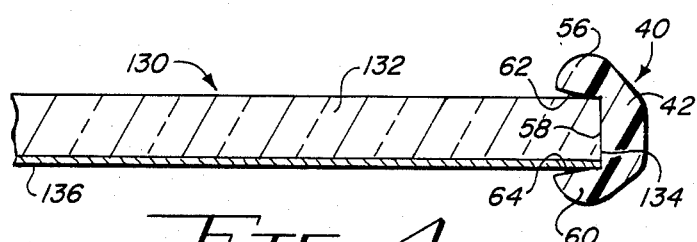
FIG. 4 is a view in partial section of a portion of the apparatus of FIG. 1, taken generally along line 4—4 of FIG. 1.

FIG. 1 comprises a perspective view of dental mirror apparatus 10 which includes a handle portion 20, a socket or holder portion 40, and a mirror element 130. The holder 40 is secured to the handle 20, and the mirror 130 is in turn secured to and held by the socket or holder 40. FIG. 2 comprises a top view of the dental mirror apparatus 10 of FIG. 1, illustrating the handle 20, including a removable tip portion 30, and its relationship to the socket or holder 40 and the mirror 130. FIG. 3 is a view in partial section of the mirror apparatus 10 of FIG. 1, taken generally along line 3—3 of FIG. 1. FIG. 4 is a view in partial section of a portion of the mirror apparatus 10 of FIG. 1, taken generally along line 4—4 of FIG. 1. For the following discussion concerning the dental mirror apparatus 10, reference will be made to FIGS. 1, 2, 3, and 4.

The dental mirror apparatus 10 preferably is made of a suitable or appropriate plastic material. Such plastic material may be used for both the handle 20 and the socket or holder 40. Included as part of the handle 20 is a stem 22 which, as shown best in FIGS. 1, 2, and 3, is formed integrally with the socket 40.

For convenience of manufacturing, the stem 22 may be molded as an integral part of the socket or holder 40. However, the outer or distal end of the handle 20 comprises a metal tip 30, shown separate from the stem 22 in FIG. 2, which provides the necessary weight and mass to enable the mirror apparatus 10 to be used as an endodontic instrument. The stem 22 terminates remotely from the socket or holder 40 in an end portion 24. The end portion 24 includes a threaded shank 26 which extends outwardly. The threaded shank 26 is preferably molded into the end 24 of the stem 22 and extends outwardly therefrom along the general longitudinal axis of the handle 20. The metal tip 30 includes a recess 32 which fits over the end 24. Thus, the end 24 is received into the recess 32 to provide a relatively snug fit between the tip 30 on the stem 22. The recess 32 acts as a cap for the end 24.

The recess 32 communicates directly with a tapped bore 34 into which the threaded shank 26 of the stem 22 extends. There is a threaded engagement between the shank 24 and the bore 34. The tip 30 is thus threadedly secured to the stem 22 to complete the handle 20. In place of the threaded engagement, the tip 30 may comprise a sheath which slips over the stem and may be cemented to or frictionally held by the handle.

It will be noted that the rendering comprising FIG. 2 is not a scale drawing of the relative length of the stem 22 or of the tip 30 of the handle 20. Rather, it is simply an illustration of the dental mirror apparatus 10 which includes a metal tip 30 secured to the distal end of a handle stem 22, remotely from a mirror element 130.

In use, the dental mirror apparatus 10 is simply reversed by the fingers of the using dentist when it is desirable to use the tip 30 as an endodontic instrument in conjunction with the use of the mirror 130. The length of the tip 30 is such as to provide a sufficient mass for endodontic purposes. It will be noted that the distal end of the tip 30 is such as to provide a sufficient mass for endodontic purposes. It will be noted that the distal end of the tip 30 is rounded as at 36 for convenience of use as well as convenience of manufacture. Moreover, an absence of sharp edges is obviously desirable.

The socket or holder 40 includes a circular rim 42 which extends completely about the outer periphery of the mirror element 130. As shown in the drawings, the rim 42 includes three pairs of inwardly extending tabs. The tabs are disposed in vertical relationship with respect to each pair, and the tabs extend generally inwardly from the rim 42 so as to overlie, and hold therebetween, a portion of the mirror element 130. The pairs of tabs are spaced apart a predetermined distance, which preferably is about an arcuate distance of 120 degrees.

Adjacent the juncture of the stem 22 of the handle 20 and the holder 40 is a pair of tabs 44 and 48, which extend inwardly from the upper and lower portions of the rim 42, respectively, and which define therebetween a groove 46. The mirror element 130 extends into the groove 46.

Spaced apart from the pair of tabs 44 and 48 are two other pairs of tabs, including an upper tab 50 and a lower tab 54, and an upper tab 56 and a lower tab 60. Each pair of upper and lower tabs includes a groove. As best shown in FIG. 4, a groove 58 is disposed between the tabs 56 and 60. The mirror element 130 is bounded by the rim 42 and is disposed between the pairs of tabs and in the grooves between the respective upper and lower tabs in each pair.

Since the handle 20 is molded integrally with the rim 42 and the pairs of tabs, the rim and the tabs are all made of an appropriate and preferably not a brittle, plastic. Rather, the plastic is one which is yieldable or deformable so that the mirror element 130 may, with sufficient force or pressure, be removed from the socket or holder 40 and may be reversed such that either side of the mirror element 130 may be used, as desired. It will be noted that since the socket or holder 40 does not include a bottom member, but only includes an outer rim, both top and bottom sides or surfaces of the mirror element 130 may actually be used as mirrors, regardless of the particular orientation of the mirror element 130 in the holder 40.

The mirror element 130 is preferably a relatively circular, thin, glass disc 132 which includes an outer peripheral edge 134. The outer edge 134 is preferably substantially perpendicular to the top and bottom faces or planes of the element 130. Both top and bottom surfaces of the element 130 are polished to provide relatively flat, or optically flat, surfaces. A reflective coating 136 is deposited on the "bottom" surface of the glass element 132, as best shown in FIGS. 3 and 4.

The reflective coating 136 provides a front surface mirror for the "bottom" of the element 130, while the upper surface of the element 130 comprises a plane surface mirror element.

The mirror element 130 may be easily removed from the socket or holder 40 by an appropriate bias against the mirror adjacent one of the tabs. It will be noted that the rim 42 extends about the outer or circumferential periphery of the mirror element, but only the tabs overlie the mirror. With three pairs of spaced apart tabs holding the mirror in place, an appropriate bias or force applied to the mirror element 130 adjacent one of the tabs of any pair of tabs will cause the tab to be bent or flexed out of the way of the mirror, thus freeing the mirror element. Once a portion of the mirror is free of a tab, the entire mirror element will then relatively easily move away from the two remaining pairs of tabs.

The camming action of the mirror element 130 against a tab is best shown in FIG. 4, which comprises an enlarged view in partial section of the mirror element 130, the rim 42, and the pair of tabs 56 and 60. The mirror 130 is shown disposed in a groove 56 which is defined between the tabs 56 and 60. The outer edge or periphery of the mirror element 130 fits into the groove 58 and is held therein by the tabs 56 and 60. It will be noted that the tabs 56 and 60 include an angled face, respectively indicated by reference numerals 62 and 64. The angled faces 62 and 64 help to retain the mirror 130 in the groove 58 of the rim 42, between the tabs 56 and 60. However, the angled faces 62 and 64 also act as cam surfaces to cause their respective tabs 56 or 60 to move away from the mirror 130 when force or pressure is applied by the mirror against either of the angled faces. Thus the inherent flexibility of the material out of which the socket or holder 40 is made permits a tab to be moved away from the mirror element in order to remove and to replace a mirror element, as desired.

Figure 6:
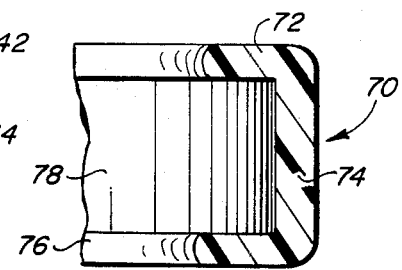
FIG. 6 is an enlarged view in partial section of a portion of the apparatus of FIG. 5, taken generally along line 6—6 of FIG. 5.
Figure 5:
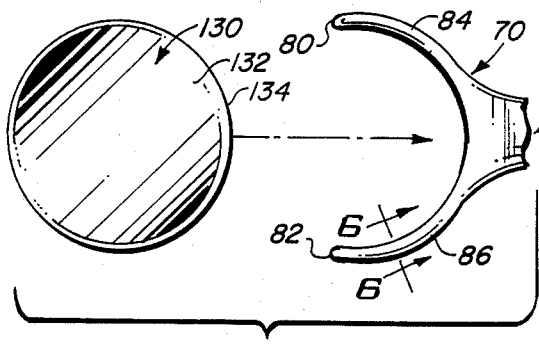
FIG. 5 is a top view of the apparatus of the present invention, showing the mirror element separated from the handle and holder element.
Figure 7:
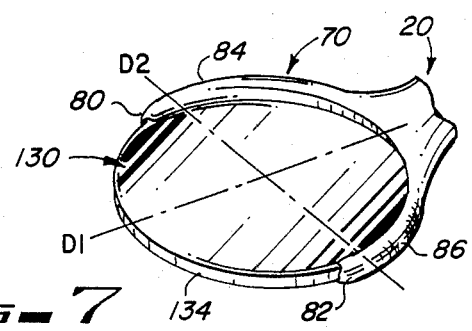
FIG. 7 is a perspective view of the mirror apparatus of FIG. 5 showing the mirror element assembled to its holder and handle element.

Another type of socket or holder apparatus, indicated by reference numeral 70, is shown in FIGS. 5, 6, and 7. The holder 70 comprises a partial circular clamp which receives the mirror element 130. FIG. 5 comprises a top view of the holder 70, with the mirror element 130 shown spaced apart therefrom. FIG. 6 comprises a view in partial section of a portion of the holder 70 of FIG. 5, taken generally along line 6—6 of FIG. 5. FIG. 7 comprises a perspective view of the holder 70 with the mirror 130 shown secured thereto. In the following discussion concerning the holder 70, reference will be made to FIGS. 5, 6, and 7.

The socket or holder 70 comprises a generally U-shaped semicircular clamp, which includes a rim 74 disposed between a pair of flanges 72 and 76. The flanges 72 and 76 are oriented substantially perpendicular to the rim 74, and they extend radially inwardly to define an inner groove 78 between the flanges and the rim 74. The mirror element 130 extends into the groove 78, with the outer peripheral edge 134 disposed within the groove 78 and against the inner portion of the rim 74.

The holder 70 terminates in a pair of outer ends 80 and 82, best shown in FIGS. 5 and 7. The holder 70 is formed of a plastic material which includes the physical properties of providing a compressive force against the elements 130 to retain it within the socket or holder 70. Accordingly, the radius of curvature of the holder 70 is slightly less than the radius of curvature of the mirror element 130. Thus, the mirror element 130 is pushed against the ends 80 and 82 of the holder 70 which causes the ends 80 and 82 to spread apart slightly to allow the mirror elements to be pushed into place within the groove 78.

As best shown in FIGS. 5 and 7, the holder 70 comprises a pair of arms 84 and 86, which extend in a curved manner from the handle 20 outwardly to terminate in the ends 80 and 82, respectively. The arms 84 and 86 are accordingly biased apart when the mirror element 130 is inserted into the holder or socket 70. The response of the arms 84 and 86 to the presence of the mirror element 130 is to apply a compressive force against the mirror to clamp the mirror securely within the socket or holder.

As best illustrated in FIG. 5, the holder 70 comprises an arcuate socket of slightly greater than 180°, or slightly more than a semi-circle. In FIG. 7, the mirror 130 is shown divided into a pair of perpendicular diametrical axes, indicated by lines D1 and D2. The diametrical axis D1 extends in general alignment with the handle 20, or longitudinally with respect to the overall mirror apparatus. The diameter D2 extends substantially perpendicular to the diameter D1, and it intersects the arms 84 and 86 between the handle 20 and the outer ends 80 and 82, respectively. The distance between the diameter D2 and the outer ends 80 and 82 is relatively small, but yet is sufficient to allow a compressive force to clamp the mirror element 130 to the holder 70.

An alternate holder or socket 90 for the mirror element 130 is illustrated in FIGS. 8 and 9. FIG. 8 is a view in partial section of the socket 90 secured to the handle 20, with the mirror element 130 disposed in the socket 90. FIG. 9 is a perspective view of the socket 90, with the mirror 130 removed therefrom. Reference will be made to both FIGS. 8 and 9 for the following discussion concerning the socket or holder 90.

The socket 90, and the lower portion of the handle 20, is preferably made of optically clear plastic. Structurally, the socket or holder 90 includes an optically clear plastic bottom portion 92, both top (upper) and bottom (lower) surfaces of which are substantially planar and parallel to each other to minimize any optical distortion. The bottom 92 is relatively thin, as will be discussed below. A cylindrical rim 94 extends upwardly from the outer portion of the bottom 92. The rim 94 defines an upwardly extending flange which, together with the bottom 92, comprises a relatively short cylinder which receives the mirror element 130.

To hold the mirror 130 into the socket or holder 90, three spaced apart tabs 96, 98, and 100 extend upwardly and inwardly from the upper or top portion of the rim 94. The tabs 96, 98, and 100 are similar to the tabs shown in FIGS. 1, 2, 3, and 4, and discussed in conjunction therewith, above. As best shown in FIG. 9, each of the tabs includes a generally horizontally extending face which is disposed on the top of the mirror element and thus holds the mirror element in place. In FIG. 8, the tab 98 is shown with a lower face 99 which is disposed against the upper or top surface of the mirror element 130. In FIG. 9, the tab 100 is shown with its lower face 101 extending radially inwardly from the rim 94.

The rim 94 includes a top surface 104, and the tabs 96, 98, and 100 extend above the top surface 104. As best shown in FIG. 8, the height or thickness of the mirror element 130 is greater than the distance from the top surface of the bottom 92 to the top 104 of the rim 94, and accordingly the mirror element extends upwardly, slightly above the top surface 104. The tabs 96, 98, and 100 also extend upwardly above the top surface 104 of the socket 90 so that their lower faces, such as the faces 97, 99, and 101 of the tabs 96, 98, and 100, respectively, are substantially flush with the top surface of the mirror element 130. In this manner, the mirror element 130 is held securely within the holder 90.

As best shown in FIG. 8, the thickness of the bottom 92 of the holder 90 is relatively thin, and the reflective coating 136 of the mirror 130 is disposed against the bottom 92. Thus, the effect of the mirror apparatus still comprises a front face mirror, using the bottom 92. The advantage of the apparatus of FIGS. 8 and 9 is that the reflective coating 136 is protected by the bottom 92. However, it is obvious that the mirror element 130 may be reversed, if desired, in the holder 90. The tabs 96, 98, and 100 are, like the tabs discussed above in conjunction with FIGS. 1-4, flexible, and accordingly will move or bend away from the mirror element to allow the mirror element to be removed and either the old element inverted or a new mirror element inserted. If the mirror element 130 is inverted, with the reflective coating up, or at the top of the holder 90, then a front surface mirror is provided at the top, with a non-surface mirror provided through the optically clear plastic bottom 92.

FIG. 10 comprises a view in partial section of alternate dental mirror apparatus in which the handle 20 includes optically clear plastic which is used as an integral part of the mirror apparatus. The handle 20 is molded with a base 110 as an integral element. The base 110 includes an upper surface 112 and a lower surface 114, both of which are substantially planar and are parallel to each other to minimize distortion. A reflective coating 136 is disposed on the top surface 112, and a relatively thin glass mirror element 140 is bonded to the reflective coating 136. Thus, a pair of mirrors, one through the optically clear glass base 114 and one through the upper glass mirror element 140, is provided. The two mirrors may be alternately used without inversion or rotation, depending on the circumstances of the use.

An alternate embodiment of the apparatus of FIG. 10 is shown in FIG. 11, which comprises a view in partial section of a handle 20 secured to an optically clear plastic mirror element 120 which has a reflective coating 136 secured to the element's upper or top side. The reflective coating 136 provides a front face mirror, and a second mirror, not a front face mirror, is provided through the optically clear plastic element 120. The handle 20 in FIG. 11 need not be fabricated from optically clear plastic, but rather may be made of any appropriate plastic material.

An alternate mirror element is shown in FIG. 12, which comprises a view in partial section through the glass mirror element 140. The glass element 140 is shown with its planar and parallel top and bottom surfaces coated with reflective coatings 136 and 138, respectively. Thus, in the embodiment of FIG. 12, two front surface mirrors are provided. The base or mirror element 112 may be secured to the holders 40 or 70, as discussed above, or it may be secured within the holder 90 of FIGS. 8 and 9, if desired.

FIG. 13 comprises a view in partial section of a plastic disc 150 with a pair of reflective coatings 136 and 138 secured to its top and bottom faces, respectively. Obviously, the top and bottom faces of the plastic disc or element 150 are substantially parallel and planar to minimize any distortion of the mirrors, the reflective coatings 136 and 138.

Like the embodiment of FIG. 12, a pair of front surface mirrors is provided by the disc 150 in the embodiment of FIG. 13. The primary difference between the mirror elements of FIGS. 12 and 13 is with the material which comprises the discs in the Figures, glass with respect to the apparatus of FIG. 12, and plastic with respect to the apparatus of FIG. 13.

The mirror element of FIG. 14, which comprises a view in partial section, includes a single reflective surface 136 disposed between a pair of discs, including a plastic lower disc or base 120, and a relatively thin glass disc or element 160. The plastic base 120 is, of course, optically clear plastic, with its upper and lower faces planar and substantially parallel.

The advantage of the mirror element of FIG. 14 is the relatively harder top or upper glass disc 160, coupled together with a lower base or optically clear plastic disc which is less expensive than the glass disc 160. This is comparable to the plastic-glass combination of the apparatus of FIG. 10. The mirrors through the glass discs comprise front surface mirrors.

An alternate embodiment of the apparatus of FIG. 14 is shown in partial section in FIG. 15. In the embodiment of FIG. 15, the optically clear plastic disc or base 120 is used again, with the reflective coating 130 disposed on one of its parallel and planar faces. However, rather than utilizing the glass disc 160 of FIG. 14, a second optically clear plastic disc 122 is secured to the upper surface of the reflective coating 136. The reflective coating 136 is thus disposed between a pair of optically clear plastic bases 120 and 122.

FIG. 16 is a perspective view of an oval mirror element 170, the mirror element 170 comprising a mirror element, which may be any of the mirror elements of FIGS. 12, 13, 14, or 15, as desired, but in an oval configuration, usable with an articulated mirror apparatus comprising a handle 220 and a socket or holder 240, pivotally secured to the handle 220, as shown in FIG. 17, or with a handle 320 and a holder 340, as shown in FIGS. 18 and 19.

FIG. 17 comprises a view in partial section showing the oval mirror element 170 secured to the holder 240. The holder 240 is pivotally secured to the handle 220. The handle 220 is substantially like the handle 20, as discussed above, which is preferably made of plastic material with a metal, endodontic tool, tip. Similarly, the holder 240 may be molded of plastic material, or, in the alternative, may be made of metal. Because the handle 220 and the holder 240 pivot or move relative to each other, the holder or socket 240 is preferably of an oval configuration, and receives the oval shaped mirror element 170 of FIG. 16.

For securing the handle 220 and the holder or socket 240 together, the handle 220 includes a relatively short upper arm 222 and a relatively short lower arm 224, which are spaced apart from each other and which together define a yoke through which a pivot pin 226 extends.

The holder 240 includes a generally oval rim 242 which is of the same general configuration as the mirror element 170. The major and minor axes of the holder 240 coincide with the major and minor axes of the mirror element 170, shown in FIG. 16 as M1 and M2, respectively. Generally along the minor axis M2 of the socket 240, there is an ear 244 which extends outwardly from the rim 242. The ear 244 is received into the yoke of the handle 220, with the arms 222 and 224 disposed respectively above and below the ear 244. The ear 244 includes an aperture or hole extending, as shown in FIG. 17, vertically through the ear 244 to receive the pivot pin 226. A pair of bushings 228 is shown disposed about the pin 226 and between the arms 222 and 224 and the ear 244 of the socket 240.

For holding the mirror element 170 into the holder 240, there are three pairs of tabs, spaced apart from each other, in an arrangement similar or comparable to the holder 40 of FIGS. 1, 2, 3, and 4. A pair of tabs 246 and 248 are shown extending inwardly over the mirror 170 in the general area of the ear 244. Another pair of tabs 256 and 258 are shown spaced apart from the tabs 246 and 248. The tabs extend inwardly from the rim 224 and over the top and bottom faces of the mirror element to allow the mirror element to be replaced and inverted, as desired. Preferably, the holder 240 is made of plastic, and the tabs are molded as integral parts of the holder 240 along with the rim 242 and the ear 244.

As is understood, there is preferably a relatively tight fit between the holder 240 and the handle 220 so that the holder 240 will not move relative to the handle 220 unless such movement is specifically desired by the user of the apparatus. The bushings 228 accordingly serve a dual function of reducing friction or wear between the handle 220 and the socket or holder 240, and of providing sufficient bias therebetween to securely hold the relative position or orientation between the handle and the holder until it is desired to move the holder, with its mirror, relative to the handle.

An alternate embodiment of the relatively movable mirror apparatus of FIG. 17 is shown in FIGS. 18 and 19. FIG. 18 comprises a view in partial section through a portion of a handle 320 and a socket or holder 340. FIG. 19 is a top view of a portion of the holder or socket 340 of FIG. 18. The socket or holder 240 is oval, and accordingly receives a mirror element, such as the mirror element 170 of FIGS. 16 and 17. Both FIGS. 18 and 19 will be referred to in the following discussion concerning the handle 320 and the holder or socket 340.

The stem 320 connects to the holder or socket 340 in a pivoting connection below the socket 340. Thus, the mirror pivots not at its edge, as in the embodiment of FIG. 17, but rather inwardly from an edge. For this reason, the handle 320 includes a rather elongated and curved stem 322 which terminates in a lower stem portion 324 disposed beneath the holder or socket 340. Adjacent the top or distal portion of the lower stem 324 is a pin 326 which secures the handle 320 and the socket 340 together.

The socket or holder 340 includes a rim 342, which is of a generally oval shape, similar to the rim 242 of FIG. 17. However, the rim 342 includes a pair of flanges, including a lower inwardly extending horizontal flange 346 and an outer vertically extending flange 348. The flanges are secured together, with the vertical flange 348 extending upwardly from the outer periphery of the flange 346. The mirror element 170 is supported on the inwardly extending flange 346, and the outer periphery of the mirror element 170 is disposed against the vertically extending flange 348.

For connecting the socket 340 to the handle 320, there is a base 350 which extends inwardly from a portion of the horizontally extending flange 346. The base includes a downwardly extending cup or recess 352. The bottom of the cup or recess 352 includes an aperture which is aligned with an aperture in the lower stem portion 324 through which the pin 326 extends. The head of the pin 326 is disposed within the cup 352 so that the mirror element 170 may be disposed wholly within the socket 340 without interference by the pin 326. Between the cup 352 and the lower stem portion 324 there is an appropriate bushing 328, similar to the bushings 228 of FIG. 17.

For holding the mirror element 170 within the socket 340, three spaced apart tabs are used. One such tab, tab 360, is shown in FIGS. 18 and 19. The tabs extend inwardly from the top or upper portion of the vertically extending flange 346 and accordingly overlie the mirror element within the holder or socket 340. As with the tabs discussed above in conjunction with the other embodiments, the tab 360, and the other tabs on the socket 349 (not shown), move or flex away from the mirror element to allow the mirror element to be removed, and replaced or inverted, as required.

Except for the portion of a mirror element covered by the inwardly extending flange 346 and the tabs, which supports the mirror within the holder 340, and the base 350, both surfaces of a mirror element secured to the holder 340 are available to the user of the dental mirror apparatus.

Figure 20:
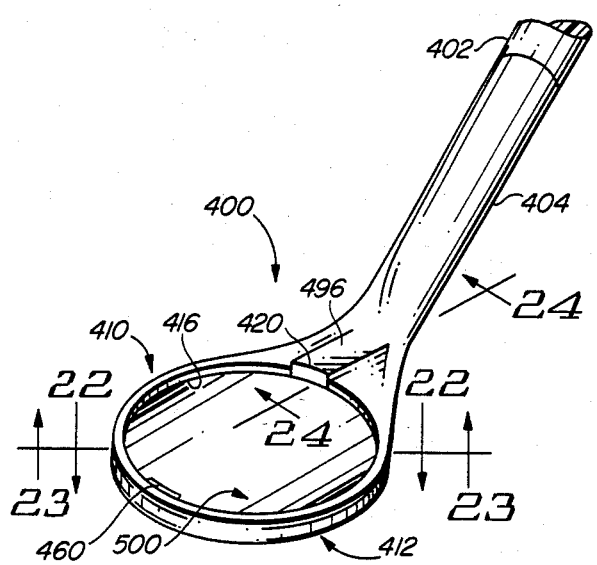
FIG. 20 is a top, front perspective view of an alternate embodiment of the apparatus of the present invention.
Figure 21:
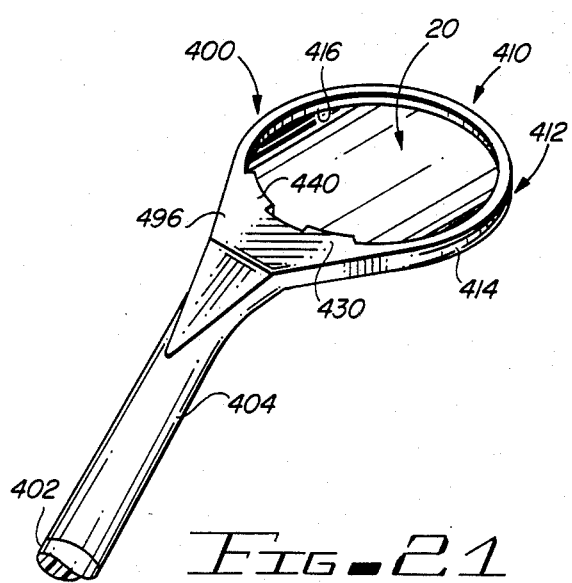
FIG. 21 is a bottom rear perspective view of the apparatus of FIG. 20.
Figure 22:
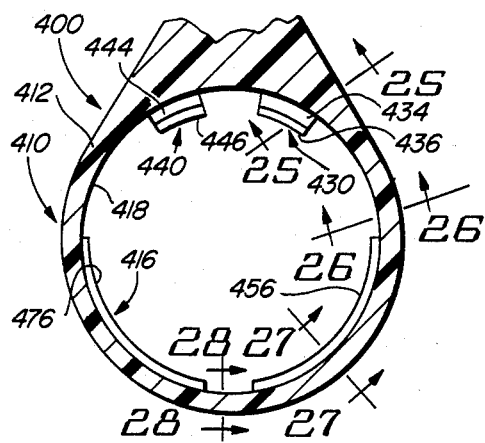
FIG. 22 is a view in partial section of the apparatus of FIG. 20, taken generally along line 22—22 of FIG. 20.

FIG. 20 is a front, top or upper perspective view of dental mirror apparatus 400, which comprises an alternate embodiment of the apparatus of the present invention. FIG. 21 is a bottom rear perspective view of the dental mirror apparatus 400 of FIG. 20. FIGS. 20 and 21 are opposite views of the mirror apparatus, with FIG. 21 showing the mirror apparatus from the top, and with FIG. 22 showing the mirror apparatus from the bottom. The mirror apparatus 400 includes a handle tip 402, which is preferably made of metal so as to comprise an endodontic tool. The tip 402 is secured to a stem 404. A holder or socket 410 is in turn secured to the stem 404, remote from the tip 402.

The holder or socket 410 includes a circular rim 412 and a connecting portion 496 which extends from the rim 412 to the handle 404. The rim 412 has an outer periphery 414 and an inner periphery 416. The inner periphery 416 is relatively irregular, and it includes a plurality of tabs, wall faces, and the like, which will be described in detail below, and a generally circular inner midline 418. The midline 418 is illustrated best in FIGS. 24-28, and will be described in detail below. The purpose of the inner, circular midline, and the various wall faces which intersect or extend from the midline 418, may best be understood by reference to FIG. 24. The inner periphery 416, including all of its wall faces and the midline 418, define a generally concave rim into which the generally convex outer rim of a mirror fits.

Figure 24:
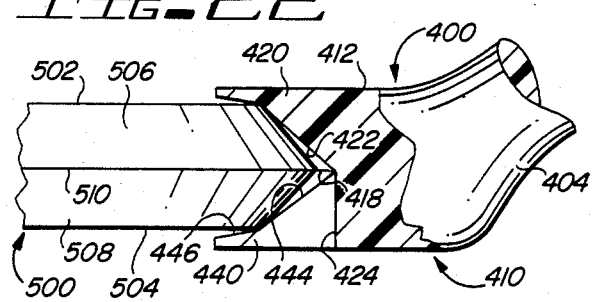
FIG. 24 is a view in partial section of the apparatus of FIG. 20, taken generally along line 24—24 of FIG. 20.

A double-faced mirror 500 is illustrated in FIG. 24. The mirror 500 includes a pair of mirror faces 502 and 504, at least one of which, and preferably both of which, are front surface mirrors. Front surface mirrors have been discussed in detail above. The mirror 500 is shown in FIG. 24 in a side, elevational view. The side, elevational view illustrates the general configuration of the mirror. The mirror 500 includes a generally convex outer periphery which is used in conjunction with the inner periphery 416 of the holder or socket 410. The outer configuration of the mirror 500 includes a pair of outwardly sloping walls 506 and 508 which terminate outwardly in a peripheral center line 510, remote from their respective faces 502 and 504. Thus, the center line 510 defines the widest diameter of the mirror apparatus 500 and defines a center line midway between the substantially parallel mirror faces 502 and 504. The center line 510 and the walls 506 and 508 define the outer periphery of the mirror 500. The angle of the faces 502 and 504 is different from the angles of the various wall faces on the inner periphery 416 of the rim 412. The wall faces on the inner periphery 416 may or may not contact the faces of the mirror, but contact, if any, is not continuous. The lack of continuity allows for the drainage of water away from the mirror surfaces. This will be discussed in more detail below.

Figure 23:
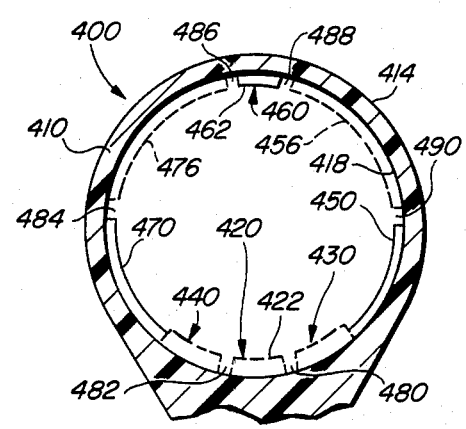
FIG. 23 is a view in partial section of a portion of the apparatus of FIG. 20, taken generally along line 23—23 of FIG. 20.

FIG. 22 comprises a plan view in partial section of a portion of the holder or socket 410 of the mirror apparatus 400 of FIG. 20, taken generally along or through the midline 418, and looking downwardly, generally along line 22—22 of FIG. 20. FIG. 23 is also a plan view in partial section of a portion of the circular rim 412 taken along the inner circular midline 418, looking upwardly, generally along line 23—23 of FIG. 20. Thus, FIGS. 22 and 23 are views through the holder or socket 410, generally on a plane through the inner circular midline 418 of the socket 410, and looking respectively downwardly and upwardly from the midline 418. For a better understanding of the cooperation of the various faces and tabs, the tabs and wall faces shown in FIG. 22 are shown in dotted line in FIG. 23.

FIGS. 24-28 are views in partial section through various portions of the socket 410, taken on the respective lines shown in FIGS, 20 and 22.

It will be noted, with respect to the various lines taken through FIG. 22, that the rim portions, comprising FIGS. 25-29, while illustratively taken from FIG. 22, which is a view of only half of the socket 410, actually comprise views through the entire rim, such as shown in FIG. 20, rather than merely the one-half rim shown in FIG. 22. The various lines for FIGS. 25-28 are illustratively taken from FIG. 22 for convenience and clarity of illustration, rather than from FIG. 20, since otherwise FIG. 20 would be rather cluttered and confused. Accordingly, FIGS. 20 and 22 should both be considered while referring to FIGS. 25-28.

FIG. 24, which is a view in partial section of the mirror apparatus 400, taken generally along line 24—24 of FIG. 20, shows the stem 404 secured to the holder or socket 410, and shows a portion of the mirror 500 disposed in the socket 410. It will be noted that the mirror 500 is generally circular and symmetrical in configuration.

The midline 418 is the widest portion, or the widest diameter portion, of the inner periphery 416 of the socket 410. The inner periphery 416 is generally irregular, as shown in detail in conjunction with FIGS. 24-28. The inner periphery 416, which is concave, generally, and irregular, matches irregularity with the convex outer periphery of the mirror 500 to hold the mirror 500 in the socket 410 securely and to allow water and moisture to drain away from the outer periphery of the mirror and from the inner periphery of the socket to prevent contamination, buildup of bacteria, etc. This provides for the complete drying of both the mirror 500 and the socket 410 by allowing moisture to drain away. The faces 506 and 508 of the mirror 500 are held by contact with the angular faces on the inner periphery 416 of the rim 412. However, contact is irregular, allowing moisture to drain away from the mirror. Also, it will be noted that the center or midline 510, the widest portion of the mirror 500, does not make contact with the inner midline 418 of the rim 412.

In FIGS. 25-28, cross sections of the socket 410, taken at various locations through the circular rim 412, are shown. The mirror 500, for purposes of clarity, is omitted from FIGS. 25-28. The showing of a portion of the mirror 500 with respect to the socket 410 in FIG. 24 illustrates the mismatch between the faces on the inner periphery 416 of the rim 412 and the convex outer surfaces of the mirror 500, as defined by the faces 506 and 508 which extend away from the center line 510. It will be noted that the outer periphery of the mirror 500 may be of a generally convexly curved configuration, if desired, rather than a relatively flat convex configuration, as exemplified by the sloping faces 506 and 508. There should still be a mismatch between the convex outer surfaces of the mirror and the concave inner periphery 416 of the rim 412 for the reasons given above. That is, for cleaning and draining purposes, as discussed above, the concave inner periphery 416 of the rim 412 preferably does not match directly with the convex outer periphery of the mirror 500. Moreover, while the mirror 500 must be held sucurely by the socket 410, the mirror must also be relatively easily removable from the socket for reversal if one surface becomes scratched, for replacement, etc.

With respect to FIG. 24, the stem 404 is shown extending outwardly and upwardly from the holder or socket 410. The socket 410 includes the circular rim 412 which has a generally convex outer periphery 414 and a generally concave and irregular inner periphery 416. Aligned with the stem 404, and extending generally inwardly from the circular rim 412 is a top or upper tab 420. As shown in FIG. 20 and in FIG. 24, the tab 420 extends radially inwardly toward the center of the rim 412 and is disposed on top of the mirror 500. The tab 420 extends slightly inwardly over or on the top surface 502 of the mirror 500. Between the tab 420 and the midline 418 is a generally straight or flat sloping face 422. The face 422 slopes upwardly and inwardly from the center line 418 to the base of the tab 420. The angle of the face 422 between the tab 420 and the center line or midline 418 is different from the angle or slope of the face 506 of the mirror 500 between its center or midline 510 and its top surface 502.

From the midline 418, a generally downwardly extending vertical face 424 extends to the bottom of the rim 412.

Figure 25:
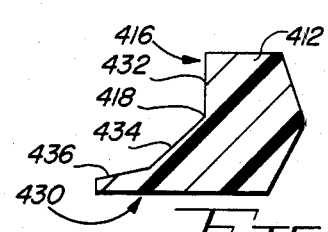
FIG. 25 is a view in partial section of a portion of the apparatus of the present invention, taken generally along line 25—25 of FIG. 22.

A pair of bottom tabs 430 and 440 (see FIG. 22 and FIG. 23) extend inwardly from the bottom or lower portion of the socket 410 on either side of the tab 420. The tabs 430 and 440 are accordingly spaced apart radially a distance which is slightly more than the radial length of the top tab 420. In FIG. 24, the tab 440 is shown adjacent to (in the background or beyond) the tab 420 and extending beneath the mirror 500, in general contact with the bottom surface 504 of the mirror 500. The tab 440 includes two sloping faces 444 and 446. The bottom surface 504 of the mirror is in contact with the face 446 of the tab 440. The tab 440 is substantially identical to the tab 430. The tab 430 is illustrated best in FIG. 25. FIG. 25 is a view in partial section through the tab 430 and the rim 412, illustratively taken generally along line 25—25 of FIG. 22.

The tab 430 extends radially inwardly from the bottom of the rim 412. The configuration of the inner periphery 416 of the rim 412 at the area of the tab 430, and which configuration is generally coextensive with the radial extent of the tab 430, is illustrated in FIG. 25. From the center line or midline 418, a vertical face 432 extends upwardly, and a sloping face 434 extends downwardly and inwardly. The tab 430 also includes a bottom sloping face 436 which extends inwardly and slightly downwardly from the bottom or lower portion of the sloping face 434. If desired, the face 436 may be generally flat or substantially perpendicular to the vertical face 432. However, it is preferred that the face 436 have a slight, gradual slope to it.

From a plane extending through the center or midline 418 of the socket 410, the faces 424 and 432, which have been defined as vertical faces, as shown in FIGS. 24 and 25, are substantially perpendicular to such plane. The sloping faces 422 and 434 of the tabs 420 and 430, respectively, both extend at substantially the same angle from the plane, but in different directions. The faces in FIGS. 26, 27, and 28 which are designated as vertical faces are also substantially perpendicular to such a plane. The faces in FIGS. 26, 27, and 28 which are designated as sloping faces are all disposed at substantially the same angle with respect to such plane, albeit some sloping faces slope upwardly, and some sloping faces slope downwardly, with respect to the center line or midline 418.

As indicated above, the tabs 430 and 440 are substantially identical in configuration, including their radial extent, or their circumferential length, with respect to the socket 410 and rim 412. Again, this is best shown in FIG. 22, and it is also shown in phantom in FIG. 23 for illustrative purposes.

The sloping face 422 of the center tab 420 is shown in FIG. 23. The tabs 430 and 440 are shown in phantom in FIG. 23. The purpose of showing the tabs 430 and 440 in FIG. 23 is to show the relative location of the tabs, and their radial or circumferential extent with respect to the inner periphery 416 of the rim 412, for comparison, and to show a plurality of spaces between the various tabs which allow moisture to drain from the surface of the mirror. The spaces will be discussed below.

It will be noted that the mirror 500 is shown in FIGS. 20 and 21, but it has been omitted from FIGS. 22 and 23 to better illustrate the location and extent of the various tabs, all of which extend radially inwardly from the rim 412. A view in cross section through the tab 440 is substantially identical to the view in partial section shown in FIG. 25 for the tab 430, which tab 430 has been discussed above.

Figure 26:
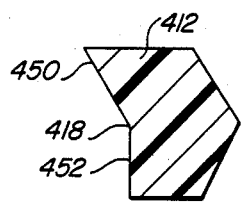
FIG. 26 is a view in partial section of the apparatus of the present invention, taken generally along line 26—26 of FIG. 22.

FIG. 26 is a view in partial section through the rim 412 spaced apart radially from the tab 430. It shows a sloping face 450 extending upwardly and inwardly from the midline 418 of the rim 412. Extending downwardly from the midline 418 is a vertical face 452. The sloping face 450 is also shown in FIG. 23. FIG. 23 also shows a sloping face 470 which is substantially identical to the sloping face 450. The sloping faces 450 and 470 are disposed adjacent to the sloping faces 434 and 444, respectively, of the tabs 430 and 440. It will be noted that the tabs 430 and 440 extend radially inwardly a slightly greater distance than do the sloping faces 450 and 470.

Figure 27:
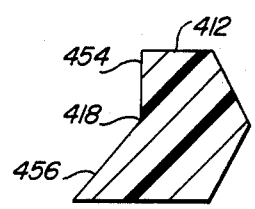
FIG. 27 is a view in partial section of a portion of the apparatus of the present invention, taken generally along line 27—27 of FIG. 22.

Disposed adjacent to the sloping faces 450 and 470, and remote from the tabs 430 and 440, are sloping faces 456 and 476, shown in FIG. 22. The cross sectional configuration of the rim 412 through the sloping face 456 is shown in FIG. 27, which comprises a view in partial section of the rim 412 taken generally along line 27—27 of FIG. 22. The sloping face 456 extends downwardly and inwardly from the midline 418. A vertically extending face 454 extends upwardly from the midline 418. A cross sectional view of the rim 412 through the sloping face 476 would be substantially identical to the configuration shown in FIG. 27.

Figure 28:
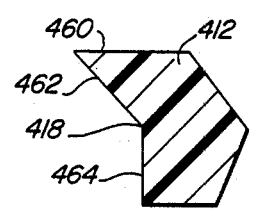
FIG. 28 is a view in partial section of a portion of the apparatus of the present invention, taken generally along line 28—28 of FIG. 22.

FIG. 28 comprises a view in partial section through the rim 412 at the front of the socket 410, taken generally along line 28—28 of FIG. 22. A tab 460 extends inwardly at the front of the socket 410, generally aligned with the tab 420. The tab 460 includes a sloping face 462 which extends upwardly and inwardly from the midline 418. A vertical face 464 extends downwardly from the midline 418. The tab 460, with its sloping face 462, and including the vertical face 464, is substantially identical, in general cross sectional configuration, to the rim 412 in the area shown in FIG. 26. This cross sectional configuration is also substantially identical to the rim portion which includes the sloping face 470, all as discussed above and as shown in FIG. 23.

As previously indicated, the sloping faces 462, 450, and 470 are substantially identical to, but inverted from, the sloping faces 456 and 476. Thus the cross sectional configurations illustrated in FIGS. 26 and 28 are the same as, but inverted from, the cross sectional configuration illustrated in FIG. 27.

Since the angles of the sloping faces of the rim 412 are different from the angular orientation of the sloping faces or outer peripheral portions of the mirror 500, the mirror 500 will have minimum physical contact with the rim 412, but yet the mirror will be held securely within the rim and within the holder or socket 410.

It will be noted that the cross sectional configurations of the tabs 430 and 440, with respect to their vertical faces and their sloping faces, are substantially identical to the cross sectional configuration of the rim 412, through the vertical face 454 and the sloping face 456 and through the sloping face 476, and its vertical face (not identified), except for the extra length of the inwardly extending portions of the tabs 430 and 440, including their inwardly extending sloping lower faces 436 and 446 which join onto the sloping faces 434 and 444.

The inner periphery 416, as discussed above, and as illustrated in FIGS. 22-28, accordingly comprises a plurality of alternating vertical faces and sloping faces which extend from a midline or center line 418. The combination of sloping faces and vertical faces allows water and moisture, etc., to be flushed away and evaporated away from the mirror for sterilization purposes and yet allows the mirror 500 to be held securely in the socket 410 for use purposes.

Referring again to FIG. 23, there are shown in phantom (dotted line) some of the inwardly extending sloping faces shown in FIG. 22. The various sloping faces shown in phantom in FIG. 23 are those shown in FIG. 22 but superimposed upon the sloping faces shown in FIG. 23 for the purpose of showing the spaces between the adjacent, peripherally extending sloping faces which comprise the inner periphery 416 of the rim 12. Six spaces 480, 482, 484, 486, 488, and 490 are shown between adjacent sloping faces. The space 480 is shown between the tab 420 and the tab 430, and a space 482 is shown between the tab 420 and the tab 440. The space 484 is shown between the sloping face 470 and the sloping face 476, while the space 486 is shown between the sloping face 476 and the tab 460. The space 488 is shown between the tab 460 and the sloping face 466, and the space 490 is shown between the sloping face 456 and the sloping face 450.

The purpose of the spaces 480 . . . 490 is to allow moisture to drain from one side of the mirror to the opposite side of the mirror. Since the center line 510 of the mirror 500, which is the widest diameter portion of the mirror 500, does not extend to the center line 418 of the rim 412, as best shown in FIG. 24, the presence of the spaces 480 . . . 490 allows moisture to drain from one side of the mirror to the other side of the mirror. In this manner, the spaces 480 . . . 490 cooperate with the various vertical and sloping faces to allow for the drainage of moisture from one side of the mirror to the other side of the mirror.

The spaces 480 . . . 490 comprise arcuate separations between the various adjacent tabs and sloping faces on the inner periphery 416 of the rim 412. Since the sloping faces extend in opposite directions from the midline 418, the actual width of the spaces is greater than it appears. The spaces actually comprise overlapping portions of the vertical faces.

The socket or holder 410 is preferably made of elastomeric (plastic) material which is deformable to the extent that the mirror 500 may be removed from the holder 410 for either inversion or replacement, as desired. With a double-sided mirror, when one side becomes scratched, etc., the mirror may simply be removed and inverted or replaced, as desired or as needed.

It will be noted that in the above description of the inner periphery 416 of the rim 412 and the socket 410, the terms "flat", "vertical", and "sloping" have been used. The FIGS. 25-28, which show the cross sectional configuration of the rim 412 and the inner periphery 416, illustrate the various terms. However, it will be understood that the socket 410, including the rim 412, is circular, and that therefore the inner periphery 416 is circular to mate with the circular mirror 500. The term "vertical" accordingly, with respect to the entire socket 410, indicates that the "vertical" faces are actually portions of a cylinder, and the term "sloping" indicates that the faces are portions of a cone. The term "flat" indicates that the faces are either cylindrical or conical, but not compoundly or spherically curved, as in the case of a section from the outer or inner periphery of a sphere, a toroid, or the like. Similarly, the term "flat" as used with regard to the outer peripheral faces 506 and 508 of the mirror 500 has the same meaning as set forth above. However, it will be noted, also as stated above, that the outer periphery of the mirror may be smoothly or spherically convex, if desired. The object of the mismatch between the outer and inner peripheries being, as stated, to hold the mirror securely and at the same time to allow thorough cleaning, draining, and drying of the assembled mirror and socket.

The pairing of the vertical and sloping faces, both vertically above and below the midline, and laterally about the inner periphery of the socket or holder, accomplishes the secure holding of a mirror whether the outer periphery of the mirror has the generally sloping configuration, as shown in FIG. 24 with respect to the mirror 500, or whether the outer periphery of the mirror has a more rounded, convex configuration.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted for specific environments and operative requirements without departing from those principles. The appended claims are intended to cover and embrace any and all such modifications, within the limits only of the true spirit and scope of the invention. This specification and the appended claims have been prepared in accordance with the applicable patent laws and the rules promulgated under the authority thereof.

What is claimed is:

1. Dental mirror apparatus comprising, in combination:
   handle means, including a stem;
   mirror means, including a first mirror and a second mirror, and at least one of which mirrors comprises a front surface mirror, and having an outer periphery;
   holder means secured to the stem of the handle means for holding the mirror means, and including
      a rim deformable for releasably holding the mirror means, an inner periphery for receiving the outer periphery of the mirror means,
a midline extending about the inner periphery, and
a plurality of faces on the inner periphery and extending generally upwardly and downwardly from the midline, including a first plurality of vertical faces and a second plurality of sloping faces alternating about the inner periphery.

2. The apparatus of claim 1 in which the holder means further includes a plurality of arcuate spaces between the plurality of faces.

3. The apparatus of claim 1 in which the holder means further includes a plurality of tabs extending inwardly from the rim for contacting the mirror means.

4. The apparatus of claim 3 in which the plurality of tabs are spaced apart arcuately from the adjacent faces.

5. The apparatus of claim 1 in which the plurality of faces on the inner periphery comprises a vertical face and an inwardly sloping face disposed adjacent to each other and extending upwardly from the midline and alternating about the inner periphery to define part of the first and second pluralities of faces.

6. The apparatus of claim 5 in which the plurality of faces further includes an inwardly sloping face and a vertical face disposed adjacent to each other and extending downwardly from the midline and alternating about the inner periphery to define another part of the first and second pluralities of faces.

7. The apparatus of claim 6 in which the sloping faces and the vertical faces which extend upwardly and downwardly from the midline are disposed in an opposite relationship with a sloping face and a vertical face, respectively, paired on opposite sides of the midline.

8. The apparatus of claim 7 in which the paired sloping and vertical faces are separated arcuately to define spaces allowing moisture to drain from one side of the mirror to the other.

9. Dental mirror apparatus comprising, in combination:
handle means;
holder means secured to the handle means, including
an inner periphery,
a midline extending along the inner periphery, and
a plurality of faces on the inner periphery spaced apart from each other and extending upwardly from the midline and downwardly from the midline, including first faces and second faces; and
mirror means disposed in the holder means and contacting the first faces.

10. The apparatus of claim 10 in which the first faces comprise a plurality of spaced apart sloping faces extending from the midline and contacting the mirror means.

11. The apparatus of claim 10 in which the second faces comprise a plurality of spaced apart vertical faces extending from the midline.

12. The apparatus of claim 11 in which a first face and a second face are paired, with one of the faces extending in one direction from the midline and the other of the faces extending in the other direction from the midline.

13. The apparatus of claim 12 in which the paired first and second faces are spaced apart arcuately from each other on the inner periphery to allow moisture to drain from the mirror means.

* * * * *